(12) United States Patent
Miyoshi et al.

(10) Patent No.: US 8,747,297 B2
(45) Date of Patent: Jun. 10, 2014

(54) ENDOSCOPIC HEART SURGERY METHOD

(75) Inventors: Shunichiro Miyoshi, Tokyo (JP);
Yoshiro Okazaki, Tokyo (JP);
Michihiro Sugahara, Tokyo (JP);
Masayuki Kobayashi, Tokyo (JP)

(73) Assignee: Olympus Corporation, Tokyo (JP)

( * ) Notice: Subject to any disclaimer, the term of this patent is extended or adjusted under 35 U.S.C. 154(b) by 292 days.

(21) Appl. No.: 12/757,210

(22) Filed: Apr. 9, 2010

(65) Prior Publication Data

US 2010/0280539 A1    Nov. 4, 2010

Related U.S. Application Data

(63) Continuation-in-part of application No. 12/714,827, filed on Mar. 1, 2010.

(60) Provisional application No. 61/244,586, filed on Sep. 22, 2009.

(30) Foreign Application Priority Data

Mar. 2, 2009    (JP) .................................. 2009-048460
Dec. 16, 2009   (JP) .................................. 2009-285073

(51) Int. Cl.
*A61B 1/00*    (2006.01)
*A61B 1/12*    (2006.01)

(52) U.S. Cl.
USPC ............................ 600/101; 600/104; 600/156

(58) Field of Classification Search
USPC .......................................... 600/101, 104, 156
See application file for complete search history.

(56) References Cited

U.S. PATENT DOCUMENTS

| 3,281,141 | A | 10/1966 | Smiley et al. |
| 3,859,985 | A | 1/1975 | Eckhart |
| 4,063,553 | A | 12/1977 | Karsh |
| 4,224,929 | A | 9/1980 | Furihata |
| 4,319,568 | A | 3/1982 | Tregoning |

(Continued)

FOREIGN PATENT DOCUMENTS

| FR | 2 914 840 | 10/2008 |
| JP | 62-035318 | 2/1987 |

(Continued)

OTHER PUBLICATIONS

International Search Report dated Dec. 7, 2010 together with an English language abstract.

(Continued)

*Primary Examiner* — Alireza Nia
(74) *Attorney, Agent, or Firm* — Scully, Scott, Murphy & Presser, P.C.

(57) ABSTRACT

It is an object to provide an endoscopic heart surgery method with which it is possible to observe an endoscopic image with a stable field of view in the pericardial space. Provided is an endoscopic heart surgery method including an inserting step of inserting an inserted portion of an endoscope into a body from the subxiphoid area and inserting the inserted portion into the pericardial space by penetrating the pericardium in the vicinity of the heart apex; a moving step of advancing the inserted portion toward the base of the heart so that the inserted portion passes through the roof of the pericardial space and is moved toward the heart apex to a treated area in the pericardial space; and an observing step of observing the treated area with the endoscope.

14 Claims, 9 Drawing Sheets

(56) References Cited

U.S. PATENT DOCUMENTS

| | | | |
|---|---|---|---|
| 4,829,448 A | 5/1989 | Balding et al. | |
| 4,884,567 A * | 12/1989 | Elliott et al. | 606/126 |
| 4,991,603 A * | 2/1991 | Cohen et al. | 607/125 |
| 5,035,231 A | 7/1991 | Kubokawa et al. | |
| 5,048,537 A | 9/1991 | Messinger | |
| 5,297,536 A | 3/1994 | Wilk | |
| 5,309,896 A | 5/1994 | Moll et al. | |
| 5,324,266 A | 6/1994 | Ambrisco et al. | |
| 5,336,252 A * | 8/1994 | Cohen | 607/119 |
| 5,400,773 A | 3/1995 | Zhu et al. | |
| 5,549,569 A | 8/1996 | Lynn et al. | |
| 5,697,916 A | 12/1997 | Schraga | |
| 5,725,525 A | 3/1998 | Kordis | |
| 5,735,791 A | 4/1998 | Alexander, Jr. et al. | |
| 5,759,150 A | 6/1998 | Konou et al. | |
| 5,968,017 A | 10/1999 | Lampropoulos et al. | |
| 6,015,382 A | 1/2000 | Zwart et al. | |
| 6,017,332 A | 1/2000 | Urrutia | |
| 6,071,295 A | 6/2000 | Takahashi | |
| 6,203,490 B1 | 3/2001 | Krajicek | |
| 6,251,093 B1 * | 6/2001 | Valley et al. | 604/97.03 |
| 6,267,717 B1 | 7/2001 | Stoll et al. | |
| 6,338,710 B1 | 1/2002 | Takahashi et al. | |
| 6,371,910 B1 | 4/2002 | Zwart et al. | |
| 6,390,976 B1 | 5/2002 | Spence et al. | |
| 6,471,644 B1 | 10/2002 | Sidor, Jr. | |
| 6,478,029 B1 | 11/2002 | Boyd et al. | |
| 6,699,259 B2 | 3/2004 | Fogarty et al. | |
| 6,701,930 B2 | 3/2004 | Benetti et al. | |
| 6,705,988 B2 | 3/2004 | Spence et al. | |
| 6,706,013 B1 | 3/2004 | Bhat et al. | |
| 6,740,082 B2 | 5/2004 | Shadduck | |
| 6,743,169 B1 | 6/2004 | Taylor et al. | |
| 6,890,295 B2 | 5/2005 | Michels et al. | |
| 7,022,118 B2 | 4/2006 | Ariura et al. | |
| 7,229,408 B2 | 6/2007 | Douglas et al. | |
| 7,394,976 B2 | 7/2008 | Entenman et al. | |
| 7,398,781 B1 * | 7/2008 | Chin | 128/898 |
| 7,399,272 B2 | 7/2008 | Kim et al. | |
| 7,485,624 B2 * | 2/2009 | Donovan | 514/1.1 |
| 7,621,867 B2 * | 11/2009 | Kura et al. | 600/137 |
| 7,914,444 B2 * | 3/2011 | Moriyama et al. | 600/113 |
| 8,002,802 B2 | 8/2011 | Abdou | |
| 8,109,903 B2 | 2/2012 | Terliuc et al. | |
| 8,246,539 B2 | 8/2012 | Hjelle et al. | |
| 8,409,078 B2 | 4/2013 | Ikeda | |
| 8,480,569 B2 | 7/2013 | Terliuc et al. | |
| 2001/0008961 A1 | 7/2001 | Hecker et al. | |
| 2002/0010388 A1 | 1/2002 | Taylor et al. | |
| 2002/0099270 A1 | 7/2002 | Taylor et al. | |
| 2004/0064138 A1 | 4/2004 | Grabek | |
| 2004/0153098 A1 | 8/2004 | Chin et al. | |
| 2004/0230099 A1 | 11/2004 | Taylor et al. | |
| 2005/0049463 A1 | 3/2005 | Arai et al. | |
| 2005/0065409 A1 | 3/2005 | de la Torre et al. | |
| 2005/0159645 A1 | 7/2005 | Bertolero et al. | |
| 2005/0209506 A1 | 9/2005 | Butler et al. | |
| 2006/0155169 A1 | 7/2006 | Bastia et al. | |
| 2006/0200002 A1 | 9/2006 | Guenst | |
| 2006/0259017 A1 | 11/2006 | Heil, Jr. et al. | |
| 2006/0287577 A1 | 12/2006 | Wendlandt | |
| 2006/0293662 A1 | 12/2006 | Boyer, II et al. | |
| 2007/0023334 A1 | 2/2007 | Hallstadius et al. | |
| 2007/0088203 A1 | 4/2007 | Lau | |
| 2007/0135686 A1 | 6/2007 | Pruitt, Jr. et al. | |
| 2007/0255100 A1 | 11/2007 | Barlow et al. | |
| 2008/0015569 A1 | 1/2008 | Saadat et al. | |
| 2008/0033467 A1 | 2/2008 | Miyamoto et al. | |
| 2008/0096165 A1 | 4/2008 | Virnicchi et al. | |
| 2008/0167621 A1 | 7/2008 | Wagner et al. | |
| 2008/0275371 A1 | 11/2008 | Hoffmann | |
| 2009/0043166 A1 | 2/2009 | Ishii | |
| 2009/0054943 A1 | 2/2009 | Qu et al. | |
| 2009/0171152 A1 | 7/2009 | Aoki et al. | |
| 2009/0299364 A1 | 12/2009 | Batchelor et al. | |
| 2009/0318759 A1 | 12/2009 | Jacobsen et al. | |
| 2010/0041949 A1 | 2/2010 | Tolkowsky | |
| 2010/0145361 A1 | 6/2010 | Francischelli et al. | |
| 2010/0191164 A1 | 7/2010 | Sasaki et al. | |
| 2010/0268029 A1 | 10/2010 | Phan et al. | |
| 2010/0317925 A1 | 12/2010 | Banchieri et al. | |
| 2011/0082452 A1 | 4/2011 | Melsky et al. | |
| 2011/0144572 A1 * | 6/2011 | Kassab et al. | 604/35 |
| 2012/0277538 A1 | 11/2012 | Okada | |
| 2012/0277796 A1 | 11/2012 | Gabelberger et al. | |
| 2012/0283766 A1 | 11/2012 | Makower et al. | |
| 2013/0012782 A1 | 1/2013 | Stearns et al. | |

FOREIGN PATENT DOCUMENTS

| | | |
|---|---|---|
| JP | 64-20836 | 1/1989 |
| JP | 2-55960 | 4/1990 |
| JP | 6507810 A | 9/1994 |
| JP | 7501959 A | 3/1995 |
| JP | 7-265321 | 10/1995 |
| JP | 8-117232 | 5/1996 |
| JP | 08-280815 | 10/1996 |
| JP | 975353 A | 3/1997 |
| JP | 9-187415 | 7/1997 |
| JP | 10234738 A | 9/1998 |
| JP | 11-276422 | 10/1999 |
| JP | 200023988 A | 1/2000 |
| JP | 2000-176011 | 6/2000 |
| JP | 2001-519212 | 10/2001 |
| JP | 2001-340462 | 12/2001 |
| JP | 2002-017854 | 1/2002 |
| JP | 2002-522116 | 7/2002 |
| JP | 2003-144378 | 5/2003 |
| JP | 2003529390 A | 10/2003 |
| JP | 2004-33525 | 2/2004 |
| JP | 2004-81852 | 3/2004 |
| JP | 2004-097391 | 4/2004 |
| JP | 2004-105226 | 4/2004 |
| JP | 2006-271831 | 10/2006 |
| JP | 2007-054333 | 3/2007 |
| JP | 2007-505680 | 3/2007 |
| JP | 3143693 | 7/2008 |
| JP | 2008-540117 | 11/2008 |
| WO | 9221295 A1 | 12/1992 |
| WO | 9309722 A1 | 5/1993 |
| WO | WO 93/09722 | 5/1993 |
| WO | WO 96/40368 | 12/1996 |
| WO | WO 97/10753 | 3/1997 |
| WO | WO 98/24378 | 6/1998 |
| WO | 9837814 A1 | 9/1998 |
| WO | WO 99/13936 | 3/1999 |
| WO | WO 99/60924 | 12/1999 |
| WO | WO 00/07530 | 2/2000 |
| WO | 0062680 A1 | 10/2000 |
| WO | WO 01/78809 A1 | 10/2001 |
| WO | WO 2004/012586 A2 | 2/2004 |
| WO | WO 2006/058434 A1 | 6/2006 |
| WO | 2008140117 A1 | 11/2008 |
| WO | WO 2008/134457 A1 | 11/2008 |
| WO | WO 2009/004777 A1 | 1/2009 |

OTHER PUBLICATIONS

Sosa et al., "A New Technique to Perform Epicardial Mapping in the Electrophysiology Laboratory", Journal of Cardiovascular Electrophysiology, Apr. 29, 2007, vol. 7, Issue 6, pp. 531-536.
International Search Report dated Oct. 26, 2010.
U.S. Office Action dated Aug. 16, 2012 issued in related U.S. Appl. No. 12/884,845.
U.S. Office Action dated Aug. 31, 2012 issued in related U.S. Appl. No. 12/871,172.
U.S. Final Office Action dated Jan. 18, 2013 issued in corresponding U.S. Appl. No. 12/871,172.
U.S. Final Office Action dated Feb. 7, 2013 issued in corresponding U.S. Appl. No. 12/884,845.
U.S. Non-Final Office Action dated Feb. 6, 2013 issued in corresponding U.S. Appl. No. 12/884,629.

(56) References Cited

OTHER PUBLICATIONS

U.S. Non-Final Office Action dated Feb. 22 2013 issued in corresponding U.S. Appl. No. 12/714,827.
Extended Supplementary European Search Report dated Feb. 5, 2013 issued in corresponding Application No. / Patent No. 10818721.2-1526 / 2481444 PCT/JP2010065851.
Extended Supplementary European Search Report dated Apr. 29, 2013 issued in Application No./Patent No. 10818652.9-1660 / 2481336 PCT/JP2010064674.
Extended Supplementary European Search Report dated Apr. 26, 2013 issued in Application No./Patent No. 10818781.6-1506 /2481355 PCT/JP2010063321.
Abstract only of WO 2005/028001.
Abstract only of WO 2006/124634.
Abstract of WO 99/19008 A1.
International Search Report dated Oct. 19, 2010.
U.S. Final Office Action dated Sep. 4, 2013 issued in corresponding U.S. Appl. No. 12/714,827.
U.S. Final Office Action dated Dec. 23, 2013 issued in related U.S. Appl. No. 12/884,629.
U.S. Non-Final Office Action dated Jan. 29, 2014 issued in related U.S. Appl. No. 12/714,827.

* cited by examiner

ENDOSCOPIC HEART SURGERY METHOD

CROSS REFERENCE TO RELATED APPLICATIONS

This application is a Continuation-In-Part Application of U.S. application Ser. No. 12/714,827 filed on Mar. 1, 2010 and claims the benefit of U.S. Provisional Application No. 61/244,586, filed Sep. 22, 2009, which is hereby incorporated by reference herein in its entirety.

BACKGROUND OF THE INVENTION

1. Field of the Invention

The present invention relates to an endoscopic heart surgery method.

2. Description of Related Art

In conventional known heart surgery methods, an endoscope is inserted into the space between the heart and the pericardium surrounding the heart (pericardial space), and the heart is treated while observing a treated area of the heart with the endoscope without cutting the chest open. For example, U.S. Patent Application Publication No. 2004/0064138 discloses a surgery method in which an endoscope and a surgical instrument are inserted into the pericardial space from separate holes formed by puncturing the pericardium, and the atrial appendage is removed while observing the operation of the surgical instrument with the endoscope. In such surgery, the endoscope is inserted into the pericardial space and the heart is observed and treated while still pulsing.

BRIEF SUMMARY OF THE INVENTION

The present invention has been made in view of the situation described above, and it is an object thereof to provide an endoscopic heart surgery method with which it is possible to observe an endoscopic image with a stable field of view in the pericardial space.

In order to achieve the above object, the present invention employs the following solution.

The present invention provides an endoscopic heart surgery method including an inserting step of inserting an inserted portion of an endoscope into a body from the subxiphoid area and inserting the inserted portion into the pericardial space by penetrating the pericardium in the vicinity of the heart apex; a moving step of advancing the inserted portion toward the base of the heart so that the inserted portion passes through the vicinity of the roof of the pericardial space and is moved toward the heart apex to a treated area in the pericardial space; and an observing step of observing the treated area with the endoscope.

BRIEF DESCRIPTION OF THE SEVERAL VIEWS OF THE DRAWINGS

FIGS. 7A to 7E show radiographic images, acquired according to a certain procedure, of the inserted portion inserted into the pericardial space in an endoscopic heart surgery method according to the present invention, in which FIG. 7A shows a state where the inserted portion is disposed in an I-shaped configuration, FIG. 7B shows a state where the bending portion is bent in the vicinity of the roof of the pericardial space, FIG. 7C shows a state where the inserted portion is rotated clockwise, and FIGS. 7D and 7E show states where the inserted portion is advanced further and disposed in an inverted U-shaped configuration.

DETAILED DESCRIPTION OF THE INVENTION

An endoscopic heart surgery method according to an embodiment of the present invention will be described below with reference to the drawings.

FIGS. 1 to 8, used as reference, show examples where a front-viewing endoscope is used as an endoscope. In an endoscopic heart surgery according to this embodiment, from the viewpoints of maneuverability in the pericardial space A and the influence on the heart B, preferably, an endoscope having an outer diameter dimension less than or equal to 6 mm is used. Furthermore, in order to acquire a sharp image, preferably, an endoscope having a CCD camera installed at the distal end thereof is used.

The endoscopic heart surgery method according to this embodiment includes an inserting step of inserting an inserted portion 1 of the endoscope from the subxiphoid area C into the pericardial space A, a moving step of advancing the inserted portion 1 in the pericardial space A to a treated area via the vicinity of the roof of the pericardial space A, an observation-space ensuring step of ensuring an observation space in the pericardial space A, a pulsation suppressing step of suppressing the pulsation of the heart B within the field of view of the endoscope, and an observing step of observing the treated area.

Figure 1:
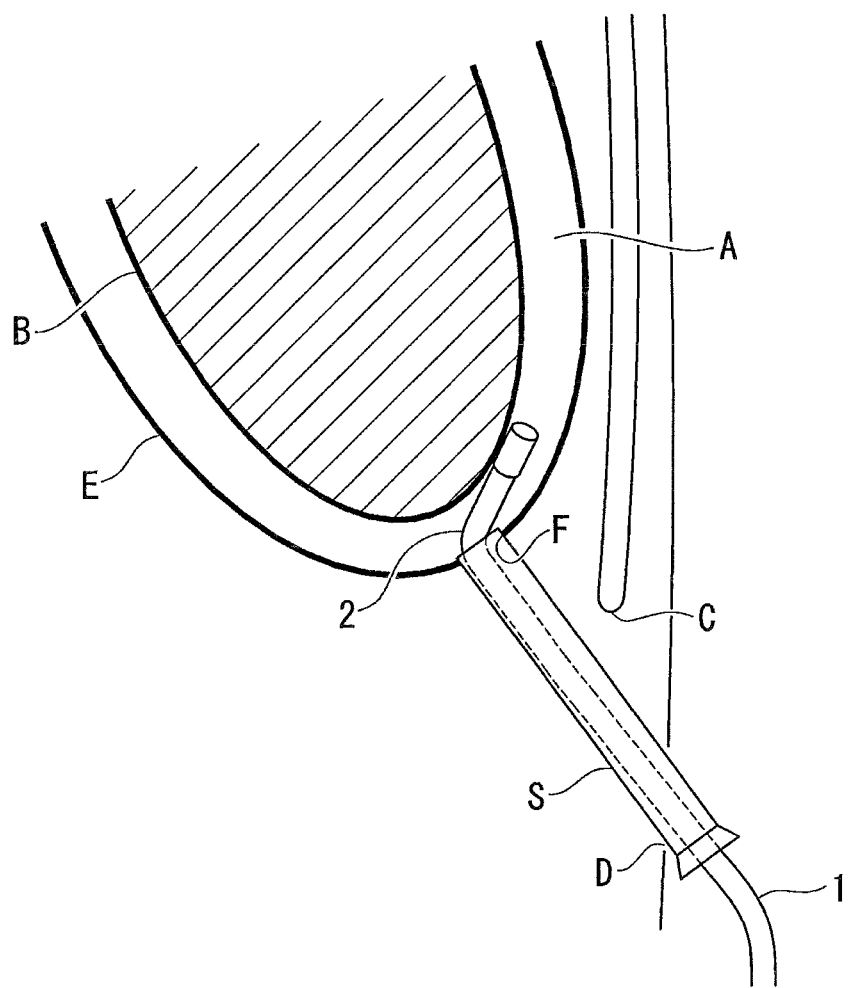
FIG. 1 is an illustration showing a state where an inserted portion is inserted into the pericardial space in an inserting step.
Figure 2:
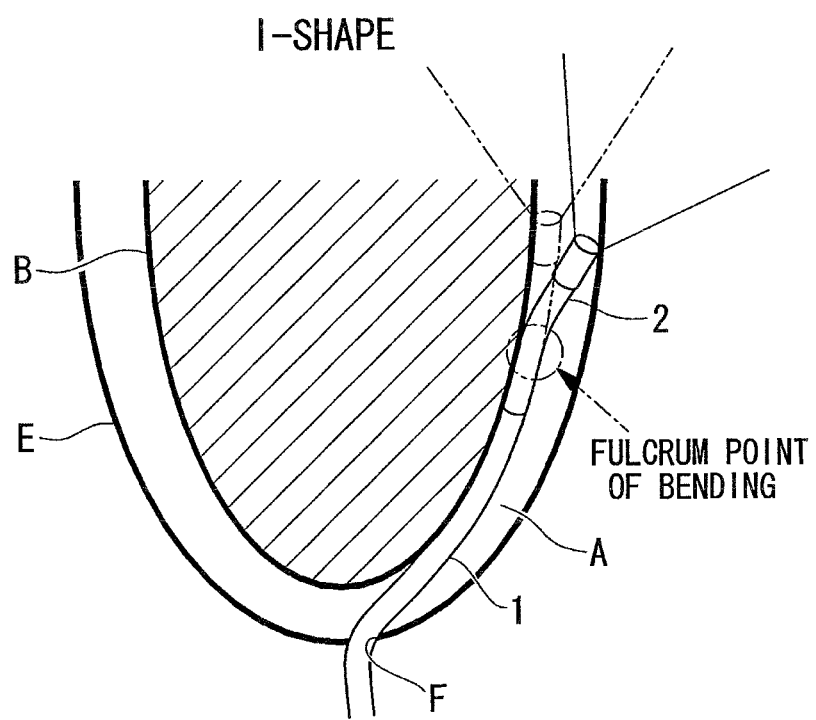
FIG. 2 is an illustration showing a state where the inserted portion is disposed in an I-shaped configuration in a moving step.

First, in the inserting step, while observing the position of the inserted portion 1 inside the body in a radiographic image, as shown in FIG. 1, the inserted portion 1 is inserted into the body via a sheath S from a hole D formed by puncturing the subxiphoid area C, and the pericardium E is penetrated in the vicinity of the heart apex. In FIG. 2 and the subsequent figures, the sheath S is omitted.

At this time, preferably, the pericardium E is penetrated with the inserted portion 1 by using the Seldinger method. That is, before inserting the inserted portion 1 through the hole at the subxiphoid area C, a puncture needle having a thin diameter is inserted from the subxiphoid area C, the pericardium E is punctured with the distal end thereof, and the puncture needle is inserted to a mid position in the pericardial space A. Then, a guide wire is inserted into the pericardial space A via a lumen formed inside the puncture needle. Then, with the guide wire remaining in the pericardial space A, the puncture needle is removed from the body. Then, the sheath S is inserted into the pericardial space A along the guide wire, and then the guide wire is removed from the body. Then, the inserted portion 1 is inserted into the pericardial space A through the inside of the sheath S. By using the serdinger method as described above, it is possible to readily introduce the inserted portion 1 into the pericardial space A from a punctured region F formed at a desired position of the pericardium E.

Figure 3:
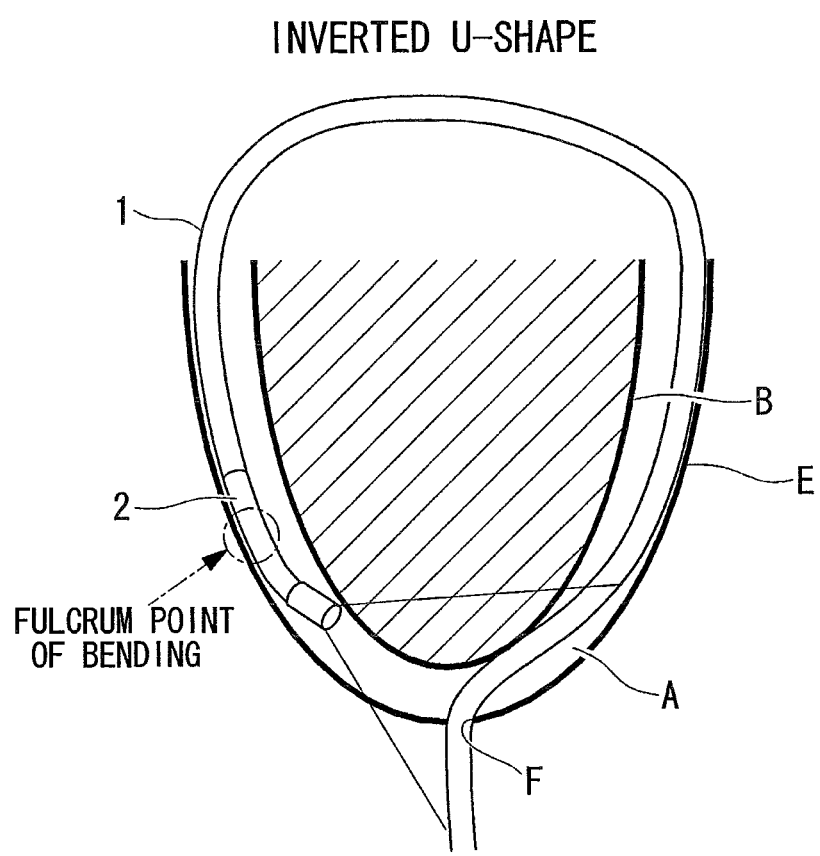
FIG. 3 is an illustration showing a state where the inserted portion is disposed in an inverted U-shaped configuration in the moving step.

Then, in the moving step, the inserted portion 1 inserted into the pericardial space A is advanced toward the base of the heart along the anterior right ventricular wall. At this time, as shown in FIG. 2, the inserted portion 1 is disposed in an I-shaped configuration following the surface of the heart B. Then, the inserted portion 1 is advanced toward the heart apex through the vicinity of the roof of the pericardial space A. Accordingly, as shown in FIG. 3, the inserted portion 1 is disposed in an inverted U-shaped configuration, so that the heart B is observed from the base of the heart towards the heart apex. In the inverted U-shaped configuration, the inserted portion 1 is abutted against the inner surface of the pericardium E by its own restoring force in an outward radial direction, by which the inserted portion 1 tends to restore its substantially linear shape. As a result, the inserted portion 1 is strongly supported by the entire pericardium E.

Here, a bending step is performed. That is, the inserted portion 1 is passed through the vicinity of the roof while bending a bending portion 2 at a maximum angle. At this time, since the bending portion 2 is bent with the pericardium E acting as a fulcrum, the distal end of the inserted portion 1 is disposed at a position away from the surface of the heart B. Thus, an appropriate observation distance is ensured between the distal end of the inserted portion 1 and the surface of the heart B, so that it is possible to observe a sharp endoscopic image of the surface of the heart B.

Figure 4:
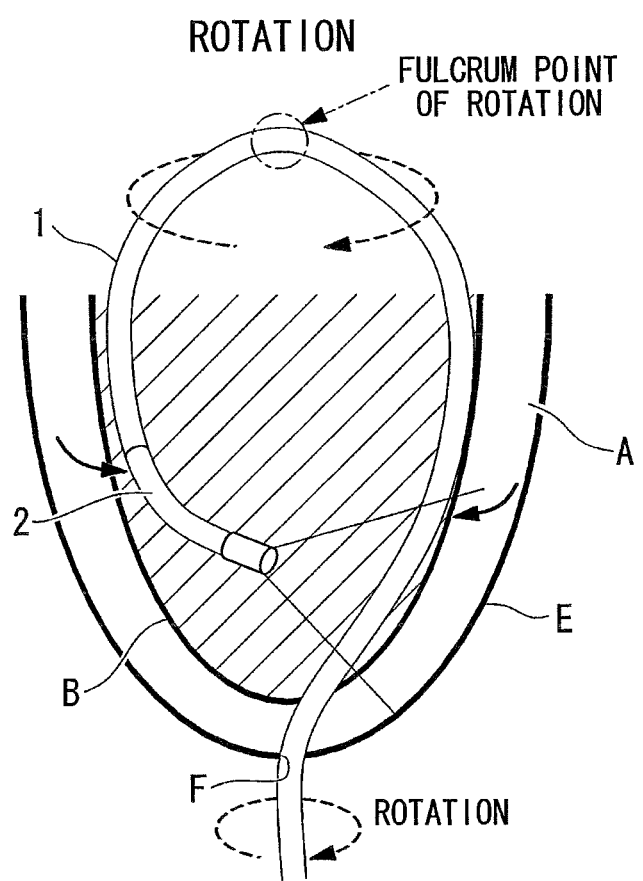
FIG. 4 is an illustration for explaining movement of the inserted portion during rotation of the inserted portion in a rotating step.

Furthermore, a rotating step is performed simultaneously with the bending step; that is, the inserted portion 1 is advanced and passed through the vicinity of the roof while rotating the inserted portion 1 in a circumferential direction. At this time, as shown in FIG. 4, the distal end of the inserted portion 1 is rotated with the roof of the pericardium E acting as a fulcrum and is moved towards the left and right sides of the heart B. Here, by choosing the rotating direction of the inserted portion 1 and adjusting the amount of rotation and the amount of insertion of the inserted portion and the bending angle of the bending portion 2, it is possible to readily move the distal end of the inserted portion to any part of the heart B. Specifically, by rotating the inserted portion 1 clockwise, it is possible to steer the distal end of the inserted portion 1 to the right atrium, the right ventricle, the right coronary artery, the right coronary vein, the right atrial appendage, the heart apex, or the anterior interventricular groove. On the other hand, by rotating the inserted portion 1 counterclockwise, it is possible to steer the distal end of the inserted portion 1 to the left atrium, the left ventricle, the left coronary artery, the left coronary vein, the coronary sinus, the left atrial appendage, the heart apex, or the posterior interventricular groove. In the case of observing the posterior left ventricular wall, preferably, the patient lies in a lateral position.

During the moving step, the orientation of the distal end of the inserted portion 1 may be confirmed by performing an orientation confirming step as needed. The orientation confirming step is performed by observing an organ adjacent to the pericardium E, for example, the lungs or the thoracic diaphragm, transparently through the pericardium E. By using these organs as landmarks, it is possible to ascertain the direction of the field of view. Alternatively, the orientation confirming step is performed by injecting a liquid into the pericardial space A via a channel formed through the inserted portion 1 and observing the position of the surface of the liquid. As the liquid, for example, physiological saline is used. Accordingly, it is possible to ascertain the vertically upward and downward directions. Preferably, the liquid is injected into the pericardial space A together with a gas. For example, 10 to 20 ml of physiological saline and 50 to 100 ml of gas are injected into the pericardial space A. Accordingly, it is possible to observe the position of the liquid surface clearly.

After disposing the distal end of the inserted portion 1 at the treated area in the moving step, a space ensuring step and a pulsation suppressing step are performed.

The space ensuring step is performed by injecting a fluid into the pericardial space A via a channel. Accordingly, the pericardium E is pushed and expanded outward, whereby the pericardial space A can be expanded. As the fluid, for example, a gas, such as carbon dioxide, is used. Preferably, the amount of the fluid injected is less than or equal to 150 ml. By expanding the pericardial space A in this manner, it is possible to ensure a distance between the distal end of the inserted portion 1 and the surface of the heart B and to observe a sharp image of the surface of the heart B.

Figure 5:
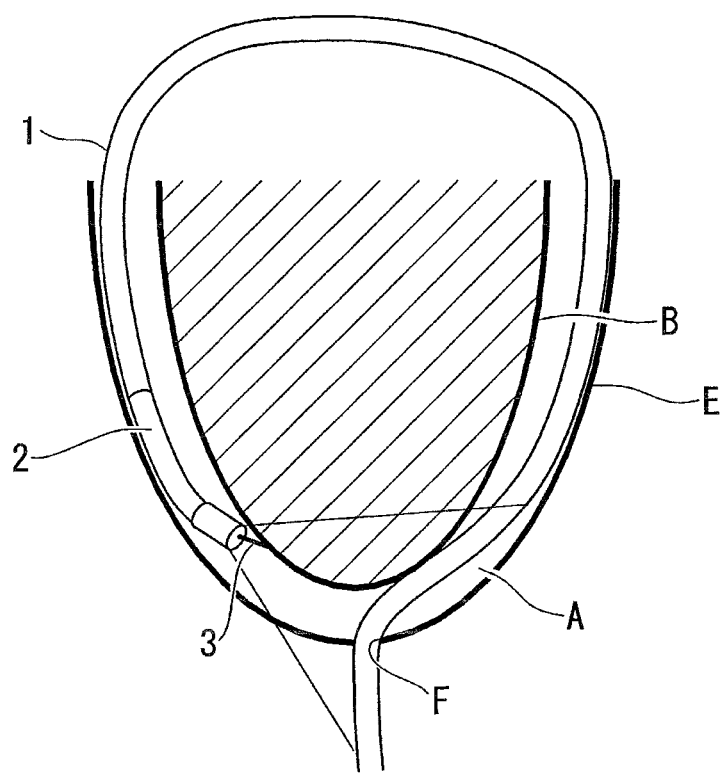
FIG. 5 is an illustration showing a state where pulsation is suppressed by a device projected from a channel in a pulsation suppressing step.
Figure 6:
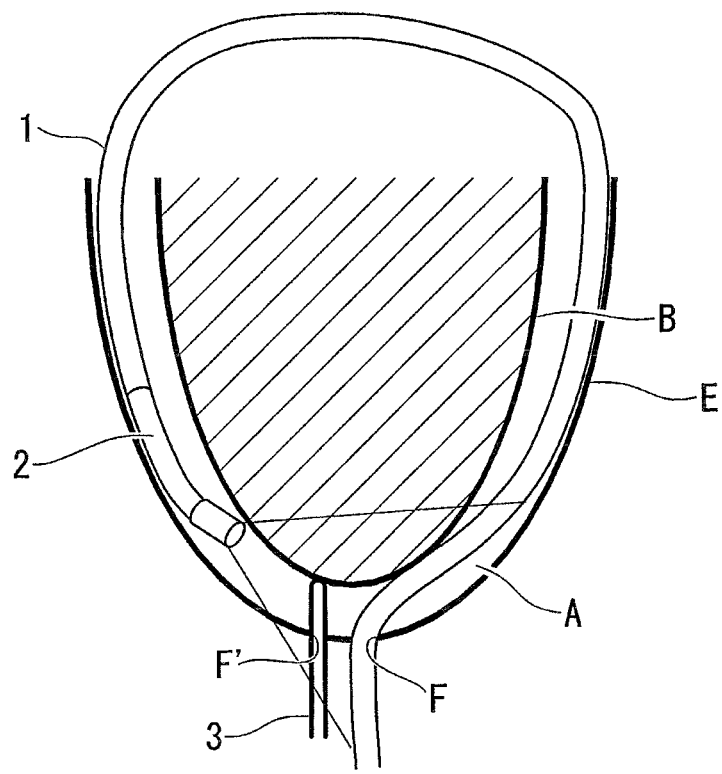
FIG. 6 is an illustration showing a state where pulsation is suppressed by a device inserted into the pericardial space from a hole different from that used for an endoscope in the pulsation suppressing step.

The pulsation suppressing step is performed by abutting against the surface of the heart B a device 3 inserted into the pericardial space A via a channel, as shown in FIG. 5. As the device 3, a tube, basket forceps, a balloon, or the like is used. Alternatively, the pulsation suppressing step is performed by inserting the device 3 into the pericardial space A from another punctured region F' formed at the pericardium E and abutting the device 3 against the surface of the heart B, as shown in FIG. 6. Accordingly, it is possible to partially suppress the pulsation of the heart B, thereby reducing movement of the treated area in the endoscopic image.

Then, in the observing step, the treated area is observed in the endoscopic image. In this step, the treated area may be treated by introducing an instrument into the pericardial space A via another channel that is different from the channel through which the device for suppressing pulsation is inserted. Alternatively, the treated area may be treated by inserting an instrument into the pericardial space A from another punctured region formed at the pericardium E.

Figure 7A:
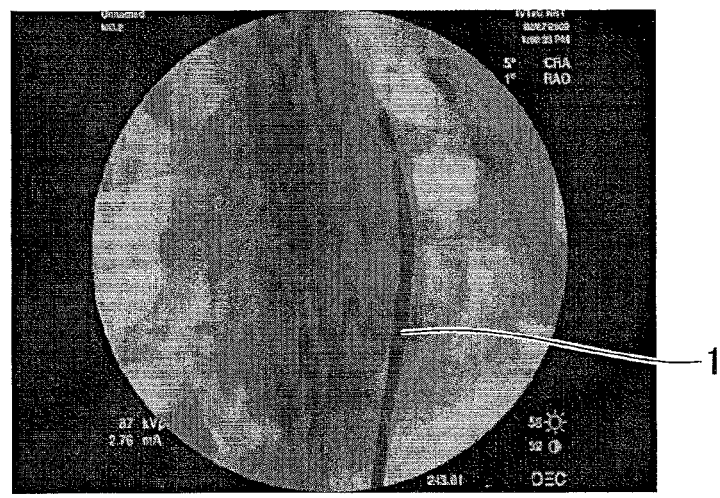
Figure 7B:
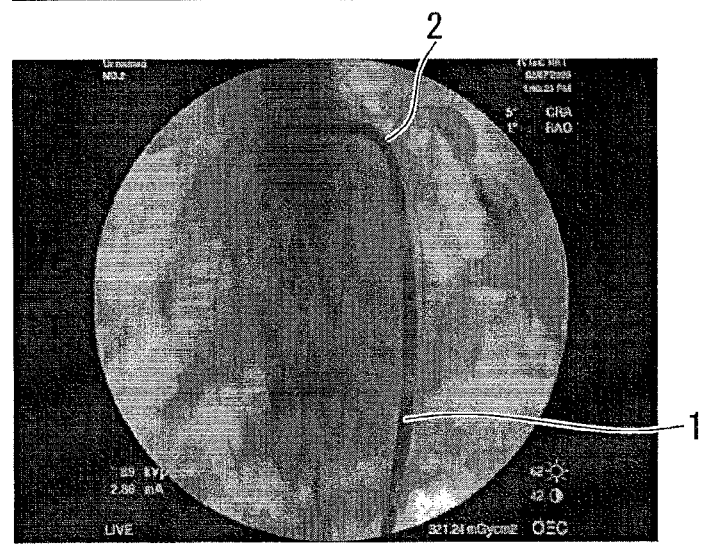
Figure 7C:
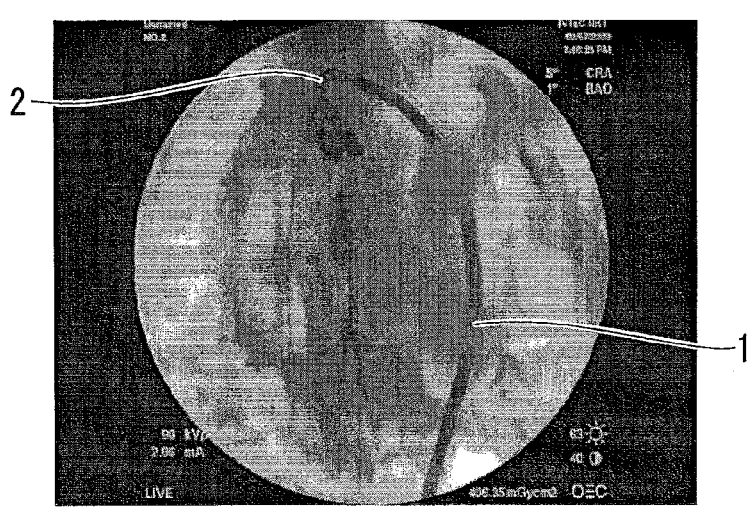
Figure 7D:
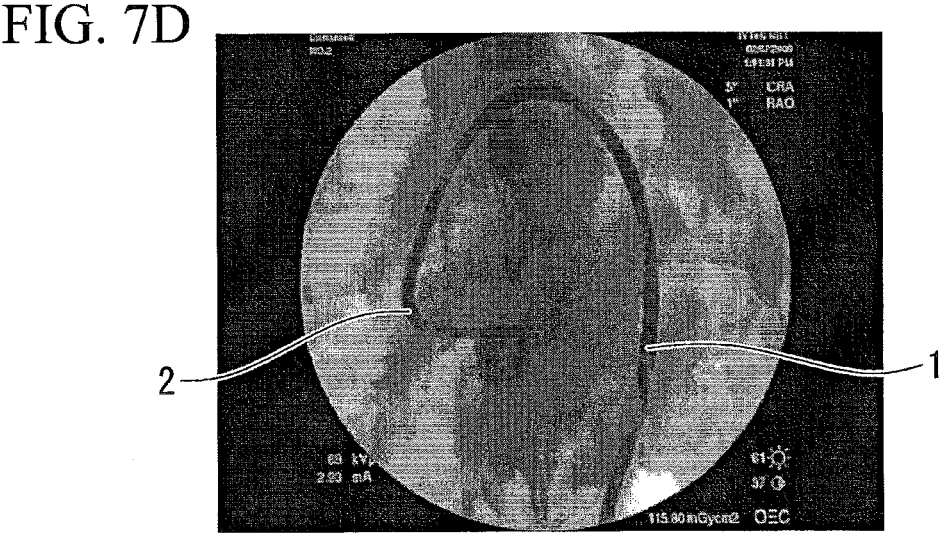
Figure 7E:
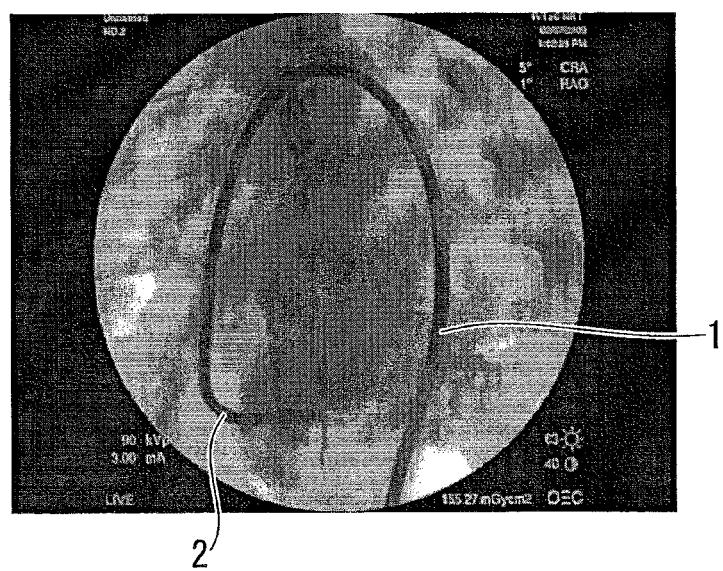

FIGS. 7A to 7E show radiographic images (fluoroscopic images) acquired by actually applying the endoscopic heart surgery method according to the present invention to the heart B of a pig. FIG. 7A shows a state where the inserted portion 1 is disposed in an I-shaped configuration. At this time, it is possible to observe the left atrial appendage and the root of the aorta. FIG. 7B shows a state where the distal end of the inserted portion 1 is trapped at the roof of the pericardial space A between the right ventricular outflow and the left atrial appendage. FIG. 7C shows a state where the bending portion 2 is bent maximally and the inserted portion 1 is advanced while rotating the inserted portion 1 clockwise. FIGS. 7D and 7E show states where the inserted portion 1 is advanced further and disposed in an inverted U-shaped configuration.

As described above, according to this embodiment, by disposing the inserted portion 1 in an inverted U-shaped configuration in the pericardial space A, the inserted portion 1 is stably supported by the pericardium E. Thus, even when the heart B is pulsing, the distal end of the inserted portion 1 is prevented from rotating or moving in an unintended direction on the surface of the heart B. Accordingly, it is possible to stably retain the distal end of the inserted portion 1 at a desired position and posture and to observe an endoscopic image with a stable position of the field of view.

Figure 8:
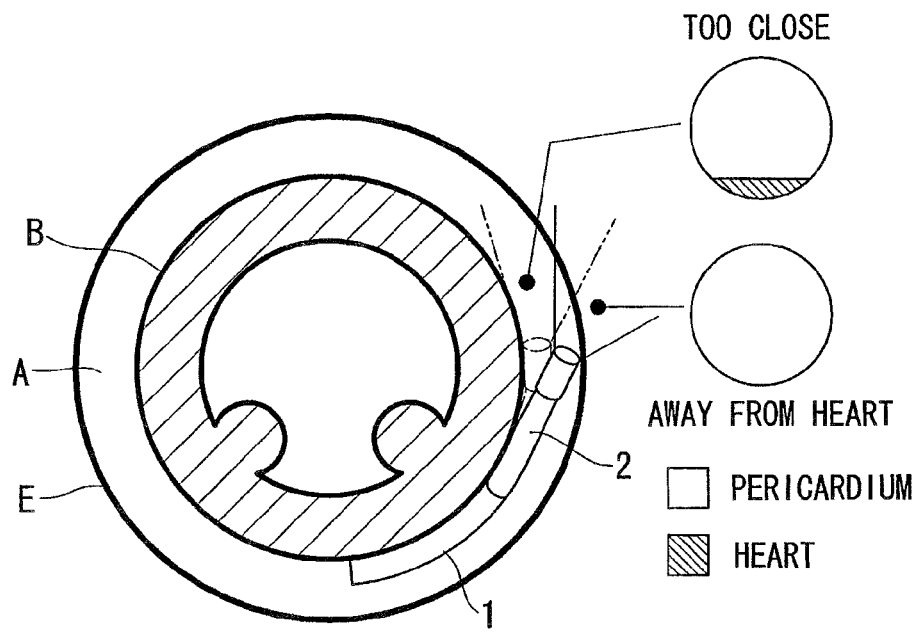
FIG. 8 is a schematic illustration showing the placement of the inserted portion and the field of view in the case of the I-shaped configuration.

Furthermore, in the case of the I-shaped configuration, as shown in FIGS. 2 and 8, the inserted portion 1 is advanced so as to slide over the surface of the heart B, and the distal end of the inserted portion 1 is oriented ahead toward the pericardium E. In this state, it is difficult to ensure an adequate distance between the distal end of the inserted portion 1 and the surface of the heart B. Thus, even if it is attempted to observe the surface of the heart B, the surface of the heart B is too close to the objective lens, so that focusing is not possible. Furthermore, the pericardium E occupies a large portion of the endoscopic image, and the heart B appears in only a part of the endoscopic image. If the bending portion 2 is bent, on the other hand, the surface of the heart B serves as a fulcrum of bending of the bending portion 2, and the distal end of the inserted portion 1 becomes separated from the surface of the heart B. Thus, the pericardium E is displayed in the entire field of view of the endoscopic image.

Figure 9:
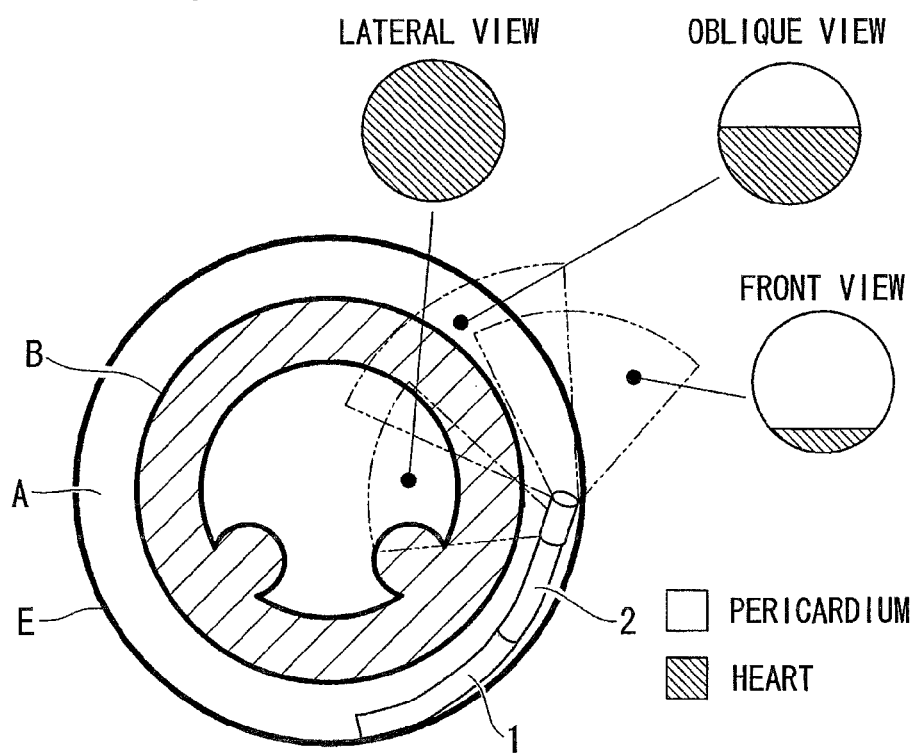
FIG. 9 is a schematic illustration showing the placement of the inserted portion and the relationship between the viewing direction and field of view of the endoscope in the case of a U-shaped configuration.

On the other hand, in the case of the inverted U-shaped configuration, as shown in FIG. 9, an adequate distance is ensured between the distal end of the inserted portion 1 and the surface of the heart B. Accordingly, it is possible to capture a sharp image of the surface of the heart B. Furthermore, by bending the bending portion 2 in this shape, it is possible to capture an image of the surface of the heart B from an angle viewing from above, thereby showing the heart B in a wider range of the endoscopic image. Furthermore, by using an endoscope with a wider viewing angle, preferably, a viewing angle wider than or equal to 120°, it is possible to observe the surface of the heart B even more readily.

In the embodiment described above, a lateral-viewing endoscope or an oblique-viewing endoscope may be used as the endoscope. By using a lateral-viewing or oblique-viewing endoscope, it is possible to readily increase the ratio of the surface of the heart B displayed in the endoscopic image, as shown in FIG. 9. As the endoscope used for an endoscopic heart surgery according to the present invention, an oblique-viewing endoscope with a viewing direction of 30° to 60° is suitable. Accordingly, it is possible to show both the surface of the heart B and the pericardium E at an appropriate ratio in the endoscopic image. In the case where a lateral-viewing endoscope is used, even though the objective lens is disposed closer to the surface of the heart B, by shaping the inserted portion 1 into an inverted U-shaped configuration, it is possible to keep the objective lens at a position away from the surface of the heart B.

The present invention has the following aspects.

The present invention provides an endoscopic heart surgery method including an inserting step of inserting an inserted portion of an endoscope into a body from the subxiphoid area and inserting the inserted portion into the pericardial space by penetrating the pericardium in the vicinity of the heart apex; a moving step of advancing the inserted portion toward the base of the heart so that the inserted portion passes through the roof of the pericardial space and is moved toward the heart apex to a treated area in the pericardial space; and an observing step of observing the treated area with the endoscope.

According to the present invention, the inserted portion inserted into the pericardial space from the vicinity of the heart apex in the inserting step is moved to the treated area via the roof of the pericardial space in the moving step, whereby the inserted portion is disposed in an inverted U-shaped configuration following the shape of the inner surface of the pericardium, so that a mid position of the inserted portion is strongly supported by the entire pericardium. Accordingly, even with the heart pulsing, it is possible to observe a desired region stably in the pericardial space with the inserted portion in a stable position and posture.

In the above invention, the moving step may include a rotating step of passing the inserted portion through the vicinity of the roof of the pericardial space while rotating the inserted portion in a circumferential direction thereof.

Accordingly, it is possible to advance the distal end of the inserted portion toward the heart apex while maneuvering it in the left and right directions of the heart with the roof of the pericardial space acting as a fulcrum.

In the above invention, the moving step may include a bending step of passing the inserted portion through the roof of the pericardial space while bending a bending portion provided at the inserted portion.

Accordingly, since the bending portion is bent with the pericardium acting as a fulcrum, an adequate observation distance is ensured between the surface of the heart and the distal end of the inserted portion. Thus, it is possible to observe an endoscopic image with proper focusing at the surface of the heart.

In the above invention, in the rotating step, the inserted portion may be rotated clockwise, and in the observing step, the right atrium, the right ventricle, the right coronary artery, the right coronary vein, the right atrial appendage, the heart apex, or the anterior interventricular groove may be observed. Alternatively, in the above invention, in the rotating step, the inserted portion may be rotated counterclockwise, and in the observing step, the left atrium, the left ventricle, the left coronary artery, the left coronary vein, the coronary sinus, the left atrial appendage, the heart apex, or the posterior interventricular groove may be observed.

As described above, by just choosing the rotating direction of the inserted portion, it is possible to readily make the distal end of the inserted portion approach a desired region of the heart.

In the above invention, the inserting step and the moving step may be performed under radiography.

Accordingly, it is possible to readily operate the endoscope while confirming the position thereof.

In the above invention, preferably, in the inserting step, the pericardium is penetrated with the inserted portion by the Seldinger method.

Accordingly, the degree of invasiveness in the pericardium is reduced.

In the above invention, there may be included a space ensuring step of ensuring a space between the pericardium and the surface of the heart prior to the observing step by injecting a fluid into the pericardial space via a channel in the inserted portion.

Accordingly, it is possible to further facilitate treatment of the treated area with an instrument.

In the above invention, there may be included an orientation confirming step of confirming the orientation of the inserted portion by observing an organ that is outside and adjacent to the pericardium transparently through the pericardium.

Accordingly, it is possible to readily confirm the orientation of the inserted portion.

Alternatively, in the above invention, there may be included an orientation confirming step of confirming the orientation of the inserted portion by injecting a liquid into the pericardial space and observing the position of the surface of the liquid.

Accordingly, since the liquid accumulates downward due to its own weight, it is possible to readily confirm the vertically upward and downward directions from the position of the liquid surface.

In the above invention, there may be included a pulsation suppressing step of suppressing the pulsation of the heart prior to the observing step by projecting a device toward the heart from a channel in the inserted portion and abutting the device against the heart.

Alternatively, in the above invention, there may be provided a pulsation suppressing step of suppressing the pulsation of the heart prior to the observing step by abutting against the heart a device that is inserted into the pericardial space by penetrating the pericardium at a position different from that of the endoscope.

Accordingly, it is possible to acquire an endoscopic image with an even more stable field of view.

In the above invention, an oblique-viewing endoscope or a lateral-viewing endoscope may be used as the endoscope.

Accordingly, it is possible to readily observe the surface of the heart even when the bending portion is not bent.

In the above invention, preferably, an endoscope having a viewing angle wider than or equal to 120° is used as the endoscope.

Accordingly, it is possible to show a wider area of the heart in the endoscopic image.

In the above invention, preferably, an endoscope with an outer diameter less than or equal to 6 mm is used as the endoscope.

Accordingly, it is possible to alleviate the stress placed on the heart.

What is claimed is:

1. An endoscopic heart surgery method comprising:
    an inserting step of inserting an inserted portion of an endoscope into a body from the subxiphoid area and inserting the inserted portion into the pericardial space by penetrating the pericardium in the vicinity of the heart apex at a first punctured region;
    a moving step of advancing the inserted portion toward the base of the heart so that the inserted portion passes through the vicinity of the roof of the pericardial space and is moved toward the heart apex to a treated area in the pericardial space;
    an observing step of observing the treated area with the endoscope; and
    a pulsation suppressing step of suppressing the pulsation of the heart prior to the observing step by abutting against the heart a rigid device that is inserted into the pericardial space by penetrating the pericardium at a second punctured region, the second punctured region being different from that of the first punctured region, wherein
    in the moving step, the inserted portion is disposed in an inverted U-shaped configuration, the entirety of which follows a shape of an inner surface of the pericardium, the inserted portion being abutted against the inner surface of the pericardium by its own restoring force in an outward radial direction, by which the inserted portion tends to restore its substantially linear shape.

2. An endoscopic heart surgery method according to claim 1, wherein the moving step includes a rotating step of passing the inserted portion through the vicinity of the roof of the pericardial space while rotating the inserted portion in a circumferential direction thereof.

3. An endoscopic heart surgery method according to claim 1, wherein the moving step includes a bending step of passing the inserted portion through the vicinity of the roof of the pericardial space while bending a bending portion provided at the inserted portion.

4. An endoscopic heart surgery method according to claim 2, wherein
    in the rotating step, the inserted portion is rotated clockwise, and
    in the observing step, the right atrium, the right ventricle, the right coronary artery, the right coronary vein, the right atrial appendage, the heart apex, or the anterior interventricular groove is observed.

5. An endoscopic heart surgery method according to claim 2, wherein
    in the rotating step, the inserted portion is rotated counterclockwise, and
    in the observing step, the left atrium, the left ventricle, the left coronary artery, the left coronary vein, the coronary sinus, the left atrial appendage, the heart apex, or the posterior interventricular groove is observed.

6. An endoscopic heart surgery method according to claim 1, wherein the inserting step and the moving step are performed under radiography.

7. An endoscopic heart surgery method according to claim 1, wherein, in the inserting step, the pericardium is penetrated with the inserted portion by the Seldinger method.

8. An endoscopic heart surgery method according to claim 1, further comprising a space ensuring step of ensuring a space between the pericardium and the surface of the heart prior to the observing step by injecting a fluid into the pericardial space via a channel in the inserted portion.

9. An endoscopic heart surgery method according to claim 1, further comprising an orientation confirming step of confirming the orientation of the inserted portion by observing an organ that is outside and adjacent to the pericardium transparently through the pericardium.

10. An endoscopic heart surgery method according to claim 1, further comprising an orientation confirming step of confirming the orientation of the inserted portion by injecting 10 to 20 ml of liquid and 50 to 100 ml of gas into the pericardial space and observing the position of the surface of the liquid.

11. An endoscopic heart surgery method according to claim 1, further comprising a pulsation suppressing step of suppressing the pulsation of the heart prior to the observing step by projecting a device toward the heart from a channel of the inserted portion and abutting the device against the heart.

12. An endoscopic heart surgery method according to claim 1, wherein an oblique-viewing endoscope or a lateral-viewing endoscope is used as the endoscope.

13. An endoscopic heart surgery method according to claim 1, wherein an endoscope having a viewing angle wider than or equal to 120° is used as the endoscope.

14. An endoscopic heart surgery method according to claim 1, wherein an endoscope with an outer diameter less than or equal to 6 mm is used as the endoscope.

* * * * *